United States Patent [19]

Shenkin

[11] Patent Number: 5,639,666
[45] Date of Patent: Jun. 17, 1997

[54] DETECTION OF RETICULOCYTES

[75] Inventor: Mark Lee Shenkin, Pembroke Pines, Fla.

[73] Assignee: Coulter Corporation, Miami, Fla.

[21] Appl. No.: 495,771

[22] Filed: Jun. 27, 1995

Related U.S. Application Data

[63] Continuation of Ser. No. 385,222, Feb. 8, 1995, abandoned, which is a continuation of Ser. No. 247,379, May 23, 1994, abandoned.

[51] Int. Cl.$^6$ .................................................. G01N 33/48
[52] U.S. Cl. .................... 436/63; 436/10; 436/17; 436/172; 435/2; 435/6; 435/34; 435/39
[58] Field of Search ........................ 436/8, 10, 16, 436/17, 63, 164, 166, 172; 435/2, 4, 6, 29, 34, 39

[56] References Cited

U.S. PATENT DOCUMENTS

| | | | |
|---|---|---|---|
| 3,872,312 | 3/1975 | Hirschfeld | 250/461.2 |
| 3,887,812 | 6/1975 | Hirschfeld | 250/458.1 |
| 3,899,297 | 8/1975 | Hirschfeld | 436/172 |
| 3,962,125 | 6/1976 | Armstrong | 436/18 |
| 3,975,084 | 8/1976 | Block | 356/335 |
| 4,325,706 | 4/1982 | Gershman et al. | 436/63 |
| 4,332,785 | 6/1982 | Allen et al. | 435/7.25 |
| 4,336,029 | 6/1982 | Natale | 436/172 |
| 4,447,547 | 5/1984 | Allen et al. | 436/543 |
| 4,571,388 | 2/1986 | O'Connell et al. | 436/63 |
| 4,707,451 | 11/1987 | Sage, Jr. | 436/63 |
| 4,822,745 | 4/1989 | Burns et al. | 436/63 |
| 4,883,867 | 11/1989 | Lee et al. | 536/25.4 |
| 4,933,293 | 6/1990 | Kuroda et al. | 436/63 |
| 4,957,870 | 9/1990 | Lee et al. | 436/63 |
| 4,971,917 | 11/1990 | Kuroda | 436/63 |
| 5,360,739 | 11/1994 | Fan et al. | 436/63 |

OTHER PUBLICATIONS

Seligman et al. *American Journal of Hematology*, vol. 14, pp. 57–66, 1983.
Lee et al. *Cytometry*, vol. 7, pp. 508–517, 1986.
Sage, Jr. et al. *Cytometry*, vol. 4, pp. 222–227, 1983.
Agrawal, Yash P. et al. Reticulocyte analysis by flow cytometry using a modified gating procedure. *Eur. Jour. Haemat.* 48(1):58–60 (1992).
Carter, John M. et al. (1989) Counting reticulocytes by flow cytometry: use of thiazole orange, *Clin. Lab. Haemat.*, 11:267–271.
Corash, Laurence et al. (1988) Enumeration of Reticulocytes Using Fluorescence–Activated Flow Cytometry, *Pathol. Immunopathol. Res.* 7:381–394.
Davis, Bruce H. et al. (1990) Clinical Flow Cytometric Reticulocyte Analysis. *Pathobiology* 58:99–106.
Davis, Bruce H. et al. (1989) Flow Cytometric Reticulocyte Quantification Using Thiazole Orange . . . Maturity Index. *Arch. Pathol. Lab. Med.* 113:684–689.
Davis, Bruce H. et al. (1993) Flow Cytometric Reticulocyte Analysis and the Reticulocyte Maturity Index. *Ann. New York Acad. Sci.* 677:281–292.
Davis, Bruce H. et al. "Clinical Flow Cytometric Reticulocyte Analysis." US and Canadian Acad. Pathology *Techniques in Diagnostic Pathology No. 2 Diagnostic Flow Cytometry* (John S. Coon and Ronald S. Weinstein, Eds.) (Williams & Wilkins).
Eder, H. et al. (1989) Automatisierte mikrofluorometrische Absolutzahlung und Reifungsanalyse von Retikulozyten. *Klin. Wochenschr.* 67:1048–1057.
Hackney, James R. et al. (1989) Automated Reticulocyte Counting by Image Analysis and Flow Cytometry. *Lab. Med.* Aug., 1989.
Hoy, T.G. "Flow cytometry: clinical applications in haematology." *Bailliere's Clinical Haematology*, vol. 3, No. 4, pp. 977–998 (1990).
Koepke, John F. (1989) Flow Cytometric Reticulocyte Counting. *Labmedica* 3:27–32.
Laharrague, P. et al. (1990) Evaluation d'un analyseur automatique de reticulocytes: le Sysmex R–1000. *Ann. Biol. Clin.* 48:253–258.
Lofsness, Karen G. et al. (1994) Evaluation of Automated Reticulocyte Counts and Their Reliability . . . Howell–Jolly Bodies. *A.J.C.P.* 101(1):85–90.
Metzger, Donna K. et al. (1987) Flow Cytometric Reticulocyte Counting With Thioflavin T in a Clinical Hematology Laboratory. *Arch.Pathol.Lab.Med.* 111:540–544.
Nobes, P.R. et al. (1990) Reticulocyte counting using flow cytometry. *J. Clin. Pathol.* 43:675–678.
Pappas, Alex A. et al. (1992) Reticulocyte Counting by Flow Cytometry A Comparison with Manual Methods. *Ann. Clin. Lab. Sci.* 22(2):125–132.
Schimenti, Kerry J. et al. (1992) Reticulocyte Quantification by Flow Cytometry, Image Analysis, and Manual Counting. *Cytometry* 13:853–862.
Serke, Stefan et al. (1993) Improved specificity of determination of immature erythrocytes . . . monoclonal antibody (anti–glycophorin–A). *Clin.Lab.Haemat.* 15:33–44.
Tatsumi, Noriyuki et al. (1989) An automated reticulocyte counting method: preliminary observations. *Med. Lab. Sci.* 46:157–160.
Tatsumi, Noriyuki et al. (1989) Inaccuracy and Imprecision of Reticulocyte Counting. *Osaka City Med. Jour.* 35(1):39–47.
Van Hove, L. et al. (1990) Reticulocyte count using thiazole orange. A flow cytometry method. *Clin. Lab. Haemat.* 12:287–299.
Wearne, Alain et al. (1985) Technical Note: Automated Enumeration of Reticulocytes Using Acridine Orange. *Pathology* 17:75–77.
Shapiro, Howard M. *Practical Flow Cytometry.* 2nd Edition, 1988, p. 144. (Alan R. Liss, Inc., New York).

*Primary Examiner*—Jill Warden
*Assistant Examiner*—Maureen M. Wallenhorst
*Attorney, Agent, or Firm*—Michelle A. Kaye

[57] ABSTRACT

A process for determining the reticulocyte population in blood samples, which process includes the use of coriphosphine O to stain reticulocytes and which process is particularly suitable for detection by flow cytometry techniques.

7 Claims, 5 Drawing Sheets

DETECTION OF RETICULOCYTES

This is a continuation of application(s) Ser. No. 08/385,222, filed on Feb. 8, 1995 entitled "Detection of Reticulocytes", now abandoned, which is a continuation of Ser. No. 08/247,379, filed on May 23, 1994 entitled "Detection of Reticulocytes", now abandoned.

BACKGROUND OF THE INVENTION

The present invention relates to the detection and enumeration of reticulocytes in a blood sample. More particularly, the present invention relates to a dye which is suitable for staining ribonucleic acid (RNA) and ribonucleic acid polymers and is particularly suitable for detecting reticulocytes by fluorescence flow cytometry techniques.

RELATED ART

Reticulocytes are immature red blood cells (RBC) from which the nucleus has been lost. Reticulocytes are known to contain RNA, and detection and enumeration of reticulocytes in a blood sample is of value to clinicians. The reticulocyte count of a blood sample has been used as an indicator of erythropoietic activity, diagnostic and prognostic value in acute hemorrhage, hemolytic anemia, and bone marrow transplantation, and as a measure of response to iron, vitamin $B_{12}$ and folic acid therapy. As known in the art, reticulocytes are precursors to mature red blood cells, and hence the term reticulocyte embraces the evolution and development of the cell whereby a mature red blood cell is generated.

In the past, reticulocytes in a blood sample have been determined by both manual and automated methods by using appropriate stains such as new methylene blue (NMB), brilliant cresyl blue (BCB), acridine orange, and pyronin Y, and thiazole orange.

Vital staining with the dye new methylene blue is considered to be the reference method for reticulocyte determinations, and in use this dye precipitates RNA. The method is manual, requires counting large numbers (for example, 500 to 1,000) of cells with a microscope, is slow, tedious, and subject to statistical errors. New methylene blue is nonfluorescent and true precipitated RNA is often difficult to differentiate from precipitated stain.

Acridine orange has had some use in staining reticulocytes by both manual and automated procedures. Acridine orange precipitates RNA; this prevents quantitative estimates of RNA content because of potential quenching. Moreover, acridine orange does not lead to a diffuse fluorescent distribution of stained cells. Age profiles of the cells (based on RNA content being proportional to fluorescence) are not reliable. Acridine orange has a great affinity for the plastic tubing in flow cytometers, which leads to increased background and lengthy procedures for removing the dye from the flow cytometer tubing. In addition, acridine orange stained cells are difficult to separate from the autofluorescent red cell peak, and the reticulocyte count is usually lower than that obtained with new methylene blue.

The use of pyronin Y requires prior fixation of the erythrocytes with formalin; this is cumbersome, time consuming, and generally yields poor results. Moreover, pyronin Y has very low quantum efficiency, leading to very low fluorescent signals.

An example of using thiazole orange for detecting reticulocytes may be found in U.S. Pat. No. 4,883,867, issued Nov. 28, 1989, which is a Continuation-In-Part of application Ser. No. 793,813, filed Nov. 1, 1985, now abandoned.

An example of using thioflavin T for detecting reticulocytes may be found in U.S. Pat. No. 4,571,388, issued Feb. 18, 1986.

Shapiro, Howard M., *Practical Flow Cytometry*, p.144, Alan R. Liss, Inc. 1985, at Table 7-3 lists tricyclic heteroaromatic compounds used for staining DNA and/or RNA. While Table 7-3 lists coriphosphine O (CPO), it does not, however, include CPO as a reticulocyte or RNA stain.

SUMMARY OF INVENTION

The present invention provides a dye and reagents incorporating such dye for the quantitative determination of reticulocytes in whole blood.

The present invention provides a process for the quantitative determination of reticulocytes wherein the dye is coriphosphine O.

The present invention further provides a method of detecting reticulocytes which includes staining a sample with coriphosphine O; exciting the sample with light of excitation wavelength; and measuring fluorescence emitted from said sample.

Also provided is a method of detecting reticulocytes wherein the sample is excited and fluorescence is measured by means of a flow cytometer.

The present invention further provides a method of differentially staining cells causing fewer interference by platelets, nucleated red blood cells, and Howell-Jolly Bodies.

The present invention provides a method of staining cells which method produces an RNA-dye complex which is more stable than complexes produced by other known methods, and which results in an increase in the time during which one can look at the total color generated by the RNA-dye complex.

DETAILED DESCRIPTION OF THE INVENTION

Figure 1:
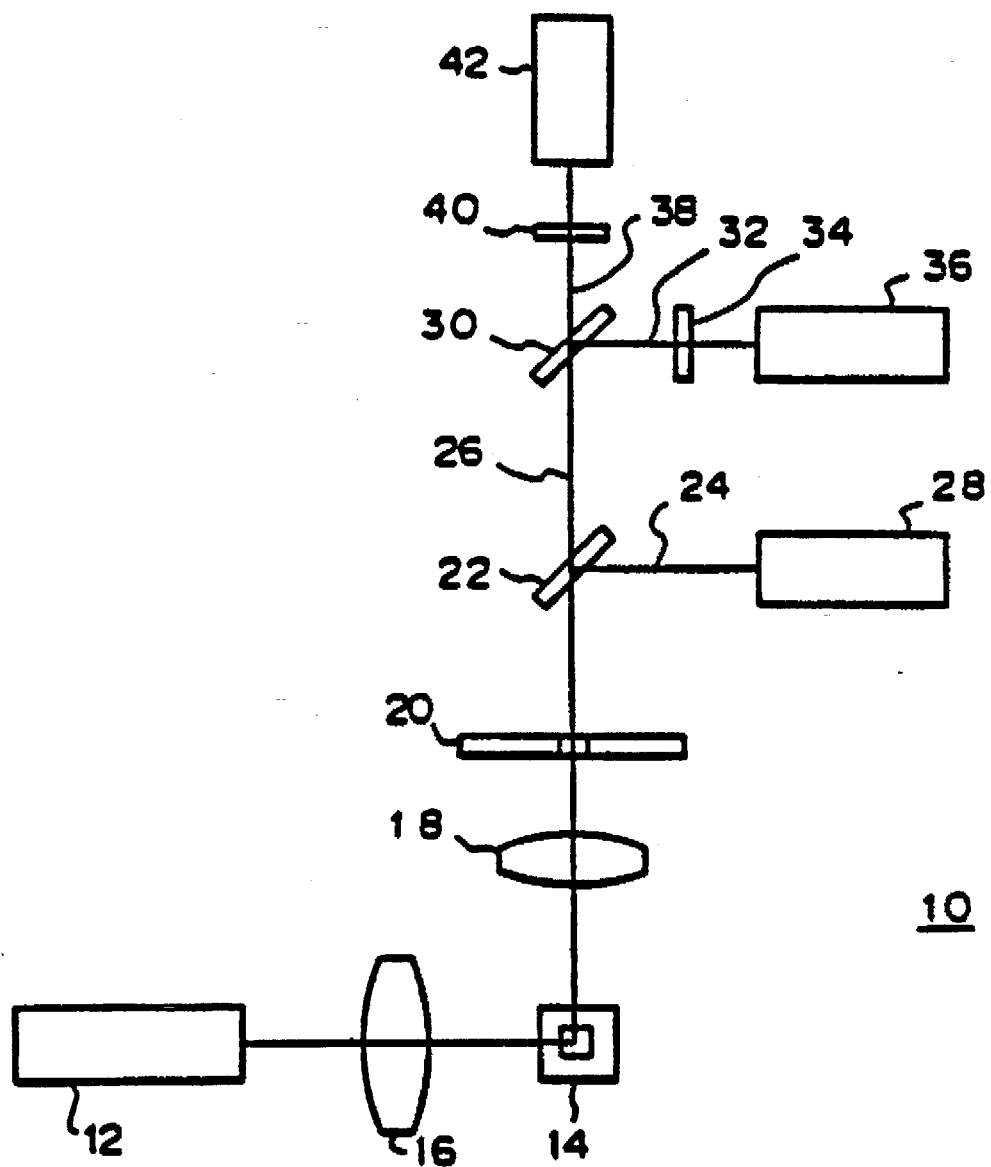
FIG. 1 shows a schematic diagram of the optics of a flow cytometer that may be employed in implementing the method of the present invention.

For convenience, the dye of the invention for staining reticulocytes is referred to as coriphosphine O (CPO), also known as basic yellow seven. Coriphosphine O is available from Pfaltz & Bauer, Inc. Division of Aceto Corporation, Waterbury, Conn.

Applicant has found that coriphosphine O is an effective dye for staining reticulocytes. The function of the reticulocyte stain is to further delineate the reticulocyte for light scatter enumeration in a flow cytometer. Thus, by using coriphosphine O as the stain, it is possible to detect and enumerate reticulocytes in a whole blood sample. Coriphosphine O is a fluorochrome dye that does not precipitate intracellular ribonucleic acid of the reticulocyte.

The use of coriphosphine O offers the advantage of differentially staining cells causing less interference by platelets, nucleated red blood cells, and Howell-Jolly Bodies. Coriphosphine O offers the further advantage of increasing stability of RNA-dye complex, thereby increasing the time during which one can look at the total color generated by the RNA-dye complex. The color generated is thus stable for a much longer period of time than dyes used in the art, for example the color generated by the use of thiazole orange is stable for about 2 hours, whereas the color generated by the use of coriphosphine O is stable for about 8 to 24 hours.

In accordance with the present invention, when staining reticulocytes in a blood sample, coriphosphine O is preferably employed as an aqueous solution, preferably in an isotonic saline solution, and most preferably in ISOTON® II, U.S. Pat. No. 3,962,125, Coulter Corporation, Miami, Fla. at CPO concentration of about 0.8 to 80 mg/L, preferably 1–40, most preferably 5–10 mg/L., which solution may contain a minor amount of methanol. The blood sample, which may be whole blood or a blood fraction, is stained with the coriphosphine O solution by mixing the blood sample with the solution of coriphosphine O. The volumes of blood sample and solution used are such that the concentrations of RBC are sufficient to run through the instrument. Thus, the concentration is in the range of 1:50–1:5000, preferably 1:100–1:1000, most preferably 1:200–1:800. The sample is then incubated for a minimum of about 60 seconds to about 8 hours, preferably 30 minutes, and then run through a flow cytometer. Applicant has found that CPO is a vital stain, and, accordingly, fixation is not required.

Coriphosphine O when unbound from ribonucleic acid (RNA) provides little or no red fluorescence, and exhibits a strong absorption peak at about 491.5 nm. When coriphosphine O is bound to RNA in the reticulocytes, the optical properties thereof change dramatically. In particular, coriphosphine O when bound to RNA in the reticulocytes exhibits a strong red fluorescence. The excitation maximum is at about 491.5 nm and the emission maximum is at about 630–700 nm, giving a Stokes shift of about 160 nm. As a result of the excitation peak of the bound coriphosphine O being in the order of about 490 nm, in using the automatic flow cytometer the light source may be a mercury lamp which has an energy line at about 485 nm or an argon ion laser which has strong emission at about 488 nm. Although excitation may be effected at other wavelengths, reticulocytes stained with coriphosphine O are preferably excited at a wavelength of from about 450 nm to about 500 nm.

Coriphosphine O when unbound to deoxyribonucleic acid (DNA) in the white blood cells provides little or no green fluorescence, whereas coriphosphine O when bound to DNA in the white blood cells exhibits a strong green fluorescence. The lack of fluorescence of the coriphosphine O dye when not bound to nucleic acid provides low background and allows an operator to select a fluorescent threshold (or "gates") for an automatic flow cytometer.

Because CPO when bound to RNA emits red fluorescence and when bound to DNA emits green fluorescence, the use of CPO offers the advantage of differentially staining cells causing fewer interference by platelets, nucleated red blood cells, white blood cells, and Howell-Jolly Bodies. This enables one to gate-in the red blood cells and thus obtain a more accurate count.

Further, when CPO is bound, the amount or intensity of green fluorescence is proportional to the amount of background or nonspecific staining due to the binding of CPO to "other" structures. These cellular structures or elements include DNA and subcellular vesicle such as lysosomes, endosomes, and granules. Each of these elements binds the CPO differently, resulting in different amounts of fluorescence. However, only single-stranded RNA will bind CPO and fluoresce only red. We determine the maximum amount of green fluorescence of mature red blood cell population as the "threshold" for both red blood cells and reticulocytes. All other cells will fluoresce green above this threshold. The difference in intensity of green fluorescence offers the advantage of differentially staining cells enabling one to gate-out non-specific cells, such as platelets and white blood cells.

Coriphosphine O dye does not precipitate RNA and, as a result, reticulocytes stained with coriphosphine O maintain a relatively homogeneous distribution of intracellular RNA, whereby there is a nearly linear relationship between the fluorescent signal measured for an individual reticulocyte and its RNA content. Clinically, this provides the physician with additional information beyond the reticulocyte count in that RNA content is a function of reticulocyte age. Accordingly, by using coriphosphine O, a clinician has the ability to obtain reticulocyte age profiles as well as simple reticulocyte counts.

In the use of coriphosphine O for staining reticulocytes in a blood sample the fluorescent signals from the stained reticulocytes are well separated from those of the mature erythrocytes, whereby results can be directly read in an automatic flow cytometer without extensive data manipulation.

Reticulocytes, RNA or DNA stained with CPO, although preferably enumerated in an automatic flow cytometer, can also be counted by a manual procedure or automated microscopy.

The fundamental concept of flow cytometry is essentially the passing of cells, one at a time, through a specific sensing region. By means of hydrodynamic focusing, single cells are passed through the sensing zone, which consists of a focused laser light source and a detection system for the measurement of scattered and fluorescent light.

Automatic flow cytometers are well known in the art, and the present invention is not limited to the use of any particular flow cytometer.

A specific example of the optics of a flow cytometer employed in the present invention is hereunder described with reference to FIG. 1. The optics shown in FIG. 1 are used in a flow cytometer designed for measuring right-angle scattered light, red fluorescence and green fluorescence. The optic generally indicated by 10 uses an argon ion laser 12 as a light source and it operates at a wavelength of 488 nm, producing an output of 15 mW. Light emitted from the laser 12 is converged by a cylindrical lens 16 and illuminates a blood sample flowing through a flow cell 14 in a conventional means.

When the stained red blood cells in the sample are irradiated by the laser light, they produce scattered light and fluorescence. The right-angle scattered light and the fluorescence are converged with a condenser lens 18 and pass through an aperture 20 to fall upon a dichroic mirror 22. The dichroic mirror 22 reflects the right-angle scattered light 24 and transmits the fluorescence 26. The right-angle scattered light 24 reflected from the dichroic mirror 22 is detected in a photomultiplier tube or photodiode 28. Of the fluorescence 26 that passes through the dichroic mirror 22, green fluorescence 32 is reflected by a dichroic mirror 30 and red fluorescence is transmitted through that mirror. The reflected green fluorescence 32 passes through a color filter 34 and is detected in a photomultiplier tube 36. The transmitted red fluorescence 38 passes through a color filter 40 and is detected in a photomultiplier tube 42.

Thus, for example, reticulocytes stained with coriphosphine O may be detected and enumerated in the COULTER® XL flow cytometer sold by Coulter Corporation, Miami, Fla. In using such automatic flow cytometers, fluorescent gates are set by use of the position of the mature red cells in the sample, and the fluorescent gates are then set to enumerate reticulocytes.

The use of an automatic flow cytometer for detection and enumeration of reticulocytes stained with coriphosphine O provides results which closely correlate with results obtained by a known standard method for enumerating reticulocytes which uses methylene blue or acridine orange, or thiazole orange.

The use of reticulocytes stained with coriphosphine O in an automatic flow cytometer is particularly advantageous in that there is low fluorescence background and fluorescent gates may be easily selected. Moreover, there is no precipitation of intracellular reticulocyte RNA, whereby the cells need not be fixed. In addition, there is a linear relationship between the fluorescent signal for an individual reticulocyte, which provides information as to reticulocyte age.

Reticulocytes stained with coriphosphine O, although preferably enumerated in an automatic flow cytometer, can also be counted by a manual procedure or automated microscopy.

Accordingly, the subject method includes the steps of:
(a) mixing a sample of blood to be tested with the subject reagent composition including the subject derivative dye composition to form a suspension of cells;
(b) incubating said suspension of cells for a time period of not less than 1 minute and not more than 24 hours at a temperature of not less than 2° C. and not more than 25° C.;
(c) measuring the derived fluorescence of the cells on a flow cytometer;
(d) generating the correlated data histograms of red fluorescence vs green fluorescence gated and light scatter (LFS vs SS);
(e) selecting the fluorescence threshold of the reticulocyte population; and
(f) calculating the total reticulocyte as percentage reticulocyte×total RBC (total RBC in billions/mL from a hematology analyzer such as the COULTER STKS (Coulter Corporation, Miami, Fla.).

The following non-limiting example illustrates various features of the present invention. The following example of the staining is utilized in obtaining the results illustrated in FIGS. 4–8.

EXAMPLE 1

Specimen was collected into triphosphate EDTA (K3EDTA). 0.002 mL of patient whole blood specimen was added to 1.0 mL of reagent. The sample was mixed and allowed to incubate at room temperature a minimum of 15 minutes but no more than 8 hours. The specimen was then mixed again just prior to analysis on a calibrated XL flow cytometer.

Figure 2:
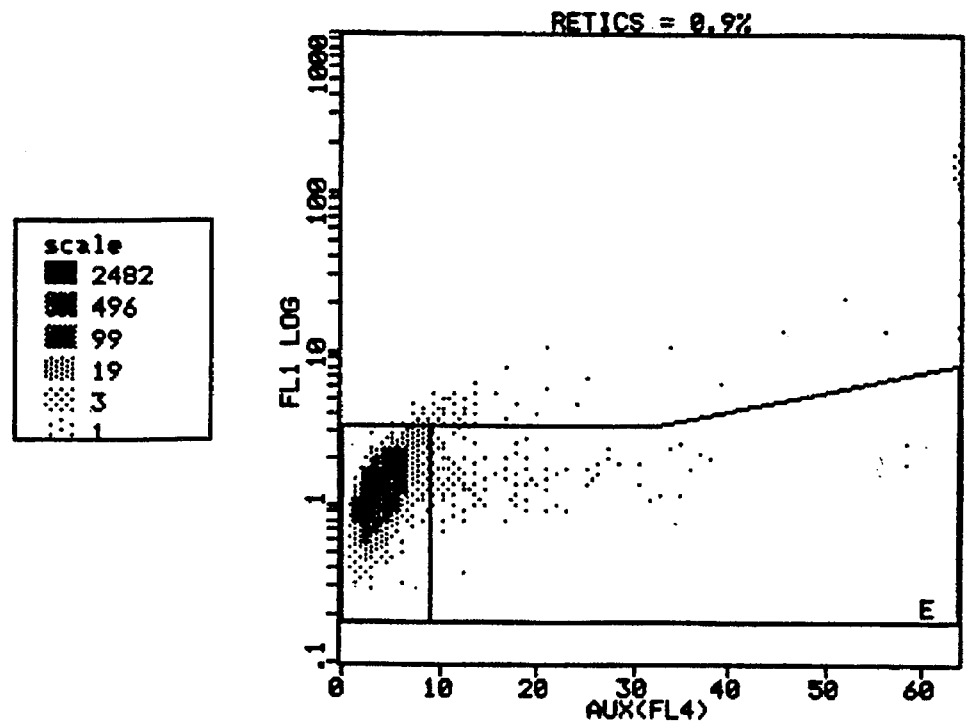
FIG. 2 shows an example of flow cytometric histogram from a normal donor.
Figure 3:
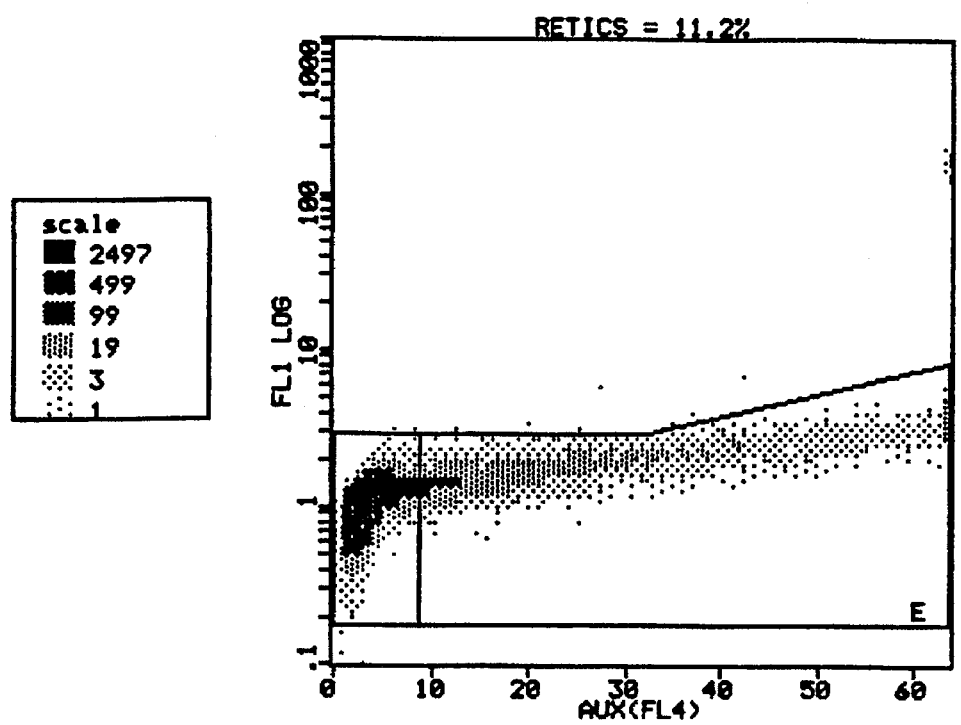
FIG. 3 shows an example of flow cytometric histogram from an abnormal (high) patient.
Figure 4:
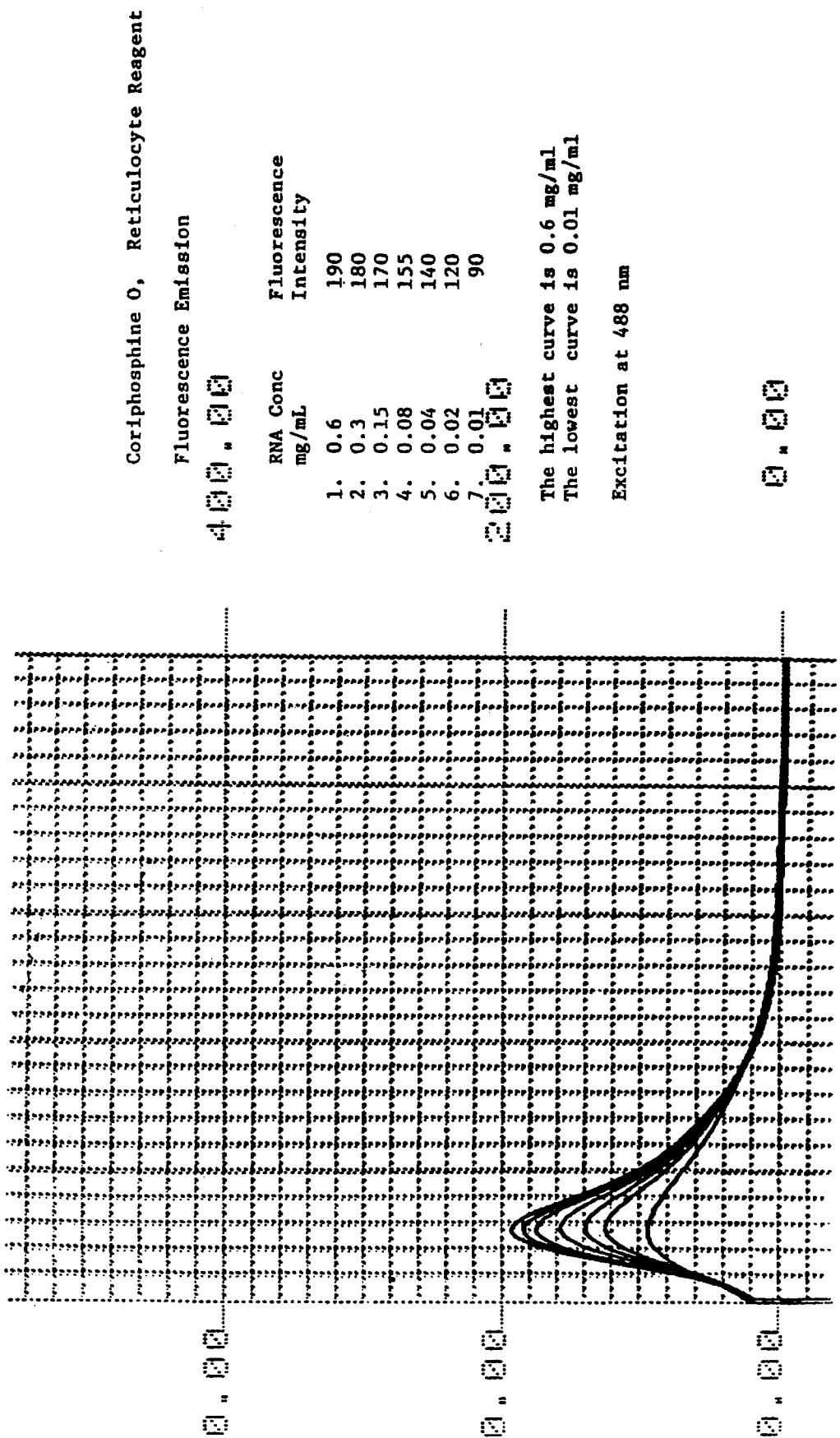
FIG. 4 shows a dose/response curve of RNA and coriphosphine O reagent.

FIGS. 2–4 show data for reticulocyte analysis of normal and abnormal blood using CPO. In particular, FIG. 2 shows a fluorescence histogram of a normal person's blood demonstrating the distribution of erythrocyte events detected by the 525 nm photomultiplier tube and by the 630 nm photomultiplier tube. As shown in FIG. 2, region E delineates the reticulocyte separate from white blood cells and platelets.

FIG. 3 shows a fluorescence histogram of an abnormal blood demonstrating the distribution of erythrocyte events detected by the 525 nm photomultiplier tube and by the 630 nm photomultiplier tube. As can be seen in FIG. 3, there is an increased number of events in the reticulocyte area (region E). As shown in FIG. 3, CPO reacts specifically with RNA, and an increase in the amount of RNA in the sample results in an increase in fluorescence.

FIG. 4 shows a graph of the dose response for the reagent when it is mixed with increasing amounts of ribonucleic acid (RNA). The more RNA that is added, the more the fluorescence intensity increases.

Figure 5:
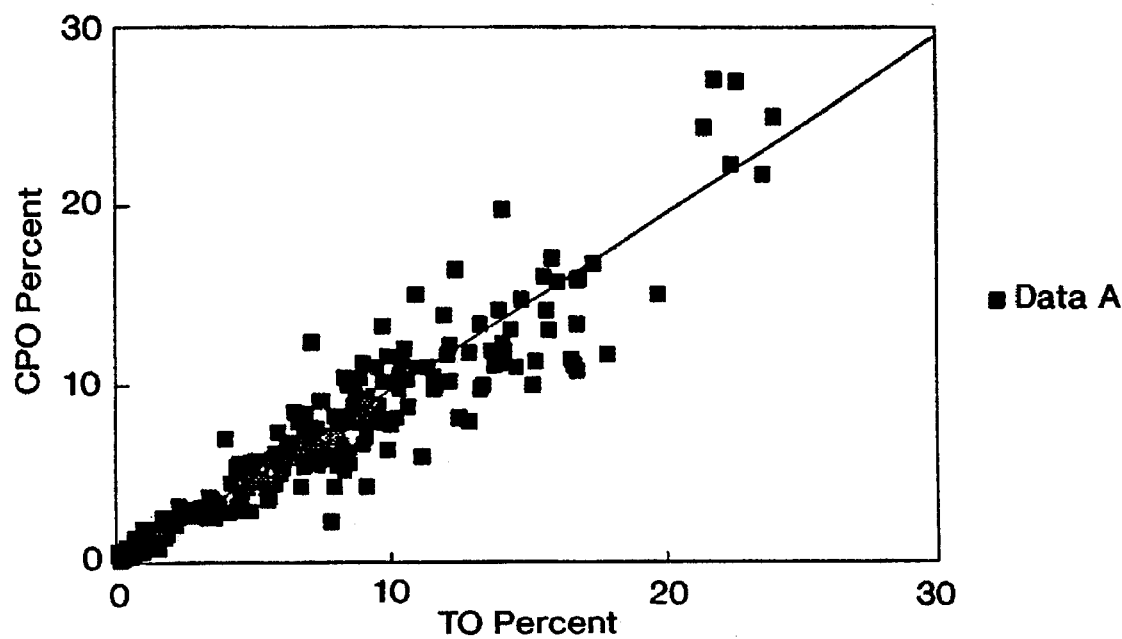
FIG. 5 shows the correlation of a CPO method of the present invention against a thiazole orange method.

FIG. 5 thus shows the correlation of a CPO method of the present invention against a thiazole orange method (reference method). As shown in FIG. 5, the results are the same for CPO as with the reference method. Thus, CPO is a measure of reticulocytes.

Figure 6:
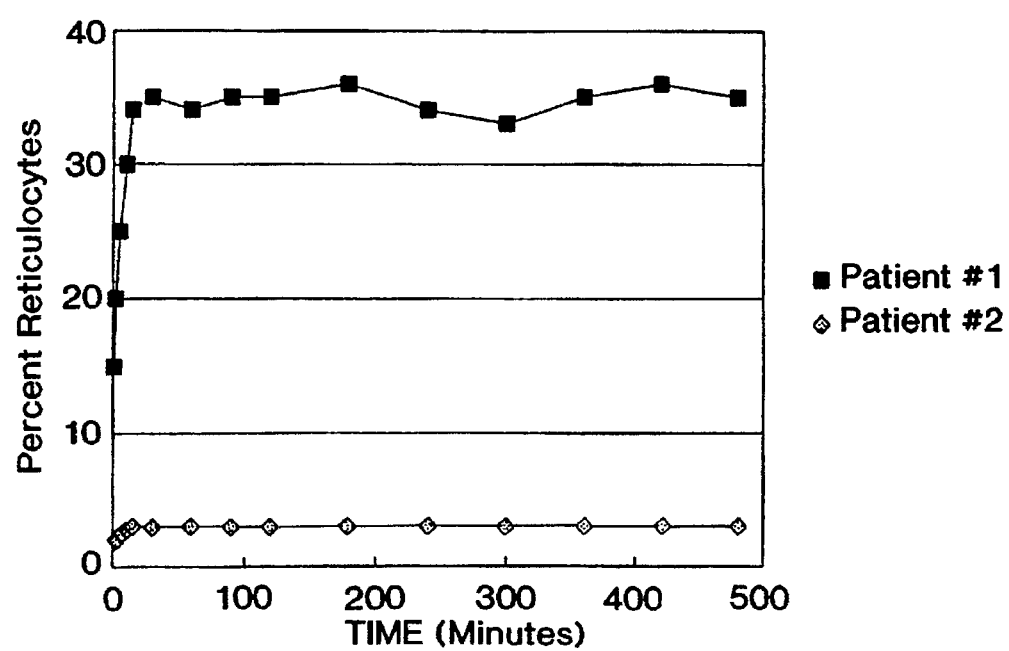
FIG. 6 shows the stability of CPO.

FIG. 6 demonstrates the stability of CPO, as a function of time versus percent reticulocytes. FIG. 6 shows that after mixing blood with reagent, it takes about 15 minutes to establish equilibrium. Once equilibrium is established, the CPO-RNA complex remains stable for at least 8 hours. Thiazole orange, acridine orange and thioflavin T, on the other hand, have a stability of less than 2 hours.

Figure 7:
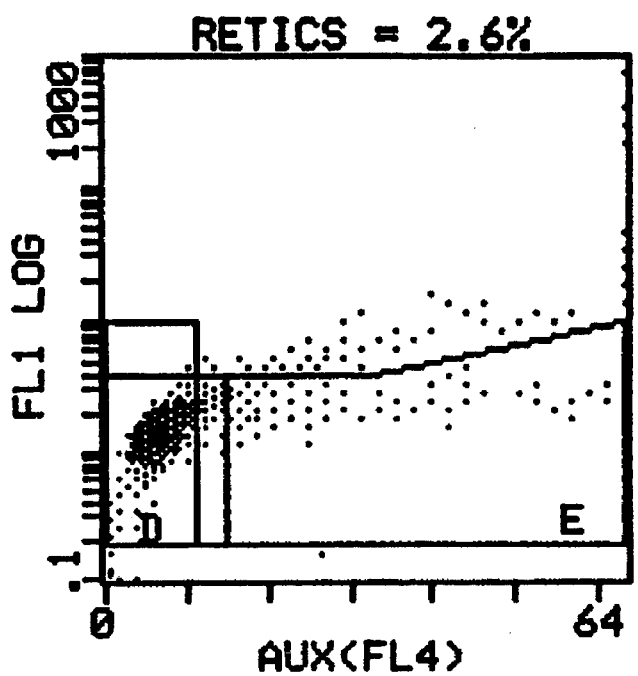
FIG. 7 gives an analysis of red blood cells and platelets.

FIG. 7 gives an analysis of red blood cells and platelets. Samples with an increased amount of platelets were used. Analysis of red blood cells and platelets shows that platelets distribution is different from reticulocytes distribution.

Figure 8:
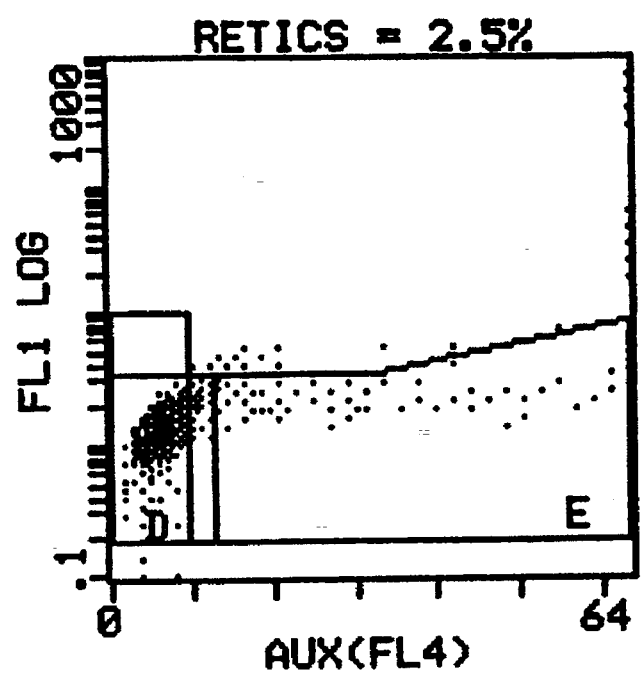
FIG. 8 gives an analysis of red blood cells and white blood cells.

FIG. 8 gives an analysis of red blood cells and white blood cells. Samples with an increased amount of white blood cells were used. Analysis of red blood cells and white blood cells shows that white blood cells distribution is different from red blood cells and reticulocytes distribution.

Numerous modifications and variations of the present invention are possible in light of the above teachings, and therefore the invention may be practiced otherwise than as particularly described.

We claim:

1. A method for quantitating reticulocytes in a sample which method comprises:
(a) combining a sample containing reticulocytes with coriphosphine O which serves to stain single-stranded RNA in reticulocytes resulting in the emission of red fluorescence and to stain DNA in non-red blood cells resulting in the emission of green fluorescence;
(b) exciting said sample with light of excitation wavelength; and
(c) measuring fluorescence emitted from said sample in order to discriminate reticulocytes containing single-stranded RNA from mature red blood cells not containing RNA.

2. A method according to claim 1, wherein the sample is excited and fluorescence is measured by means of a flow cytometer.

3. A method according to claim 2, wherein the sample is excited in the flow cytometer with light from a mercury arc lamp.

4. A method according to claim 2, wherein the sample is excited in the flow cytometer with light from an argon laser.

5. A method according to claim 1, wherein the sample is excited and fluorescence is measured by means of fluorescence microscopy.

6. A method according to claim 1, wherein the sample being analyzed comprises whole blood.

7. A method for quantitating reticulocytes in a whole blood sample by flow cytometry which comprises the steps of:
   (a) mixing a sample of blood containing reticulocytes with a reagent comprising an aqueous solution of coriphosphine O, to form a diluted suspension of cells;
   (b) incubating said sample, with said reagent, for up to 24 hours at a temperature of not less than 2° C. and not more than 25° C. in order to allow the reagent to stain single-stranded RNA in the reticulocytes, and DNA in non-red blood cells;
   (c) passing the suspension through a flow cytometer;
   (d) measuring the presence of red fluorescence in the suspension, against the presence of green fluorescence gated on light scatter in order to eliminate non-red blood cells by gating out the non-red blood cells measured by the green fluorescence; and
   (e) determining the amount or percentage of red blood cells containing single-stranded RNA in the sample from said measurement, by measuring the red fluorescence.

* * * * *